US00PP31434P2

(12) United States Plant Patent
Hansen

(10) Patent No.: US PP31,434 P2
(45) Date of Patent: Feb. 4, 2020

(54) ***SALVIA* PLANT NAMED 'PERFECT PROFUSION'**

(50) Latin Name: *Salvia nemorosa*
Varietal Denomination: Perfect Profusion

(71) Applicant: Hans A Hansen, Zeeland, MI (US)

(72) Inventor: Hans A Hansen, Zeeland, MI (US)

(73) Assignee: Walters Gardens Inc., Zeeland, MI (US)

( * ) Notice: Subject to any disclaimer, the term of this patent is extended or adjusted under 35 U.S.C. 154(b) by 0 days.

(21) Appl. No.: 16/350,492

(22) Filed: Nov. 21, 2018

(51) Int. Cl.
*A01H 5/02* (2018.01)
*A01H 6/50* (2018.01)

(52) U.S. Cl.
USPC ..... Plt./475
CPC ..... *A01H 6/508* (2018.05)

(58) Field of Classification Search
USPC ..... Plt./475
CPC ..... A01H 6/00; A01H 5/02; A01H 6/508
See application file for complete search history.

*Primary Examiner* — Keith O. Robinson

(57) ABSTRACT

A new and distinct cultivar of perennial *Salvia* plant named 'Prefect Profusion' characterized by its narrow icy blue flowers in densely arranged in verticils. The new plant has a compact habit with stiff, upright, heavily-branched stems with strong tendency to repeat when deadheaded, a strong vigorous growth rate and rugose gray-green foliage.

1 Drawing Sheet

Botanical denomination: *Salvia nemorosa.*
Cultivar designation: 'Perfect Profusion'.

STATEMENT REGARDING PRIOR DISCLOSURES UNDER 37 CFR 1.77(b)(6)

The first public disclosure of the claimed plant, in the form of a sale, was made by Walters Gardens, Inc. on Apr. 10, 2018. Prior to that, on Dec. 1, 2017 the claimed plant was displayed with a photograph and brief description in a website operated by Walters Gardens, Inc., who obtained the plant and all information relating thereto, from the inventor. No plants of *Salvia* 'Perfect Profusion' have been sold, in this country or anywhere in the world, nor has any disclosure of the new plant been made, more than one year prior the filing date of this application, and such sale or disclosure within one year was either derived directly or indirectly from the inventor.

BACKGROUND OF THE INVENTION

The present invention relates to a new and distinct cultivar of ornamental sage plant hereinafter referred to by the cultivar name *Salvia* 'Perfect Profusion' or as the new plant. The new plant was selected as a single seedling from a cross made on May 17, 2012 at a wholesale perennial nursery in Zeeland, Mich. with 'Crystal Blue' U.S. Plant Pat. No. 26,344 as the female or seed parent with 'Sensation Deep Rose' (not patented) as the male or pollen parent. Seeds were collected in the summer of 2012 and the new plant begun the trial phase in the summer of 2014 and eventually assigned the breeder code 12-59-2 prior to assigning a cultivar name.

The new *Salvia* was further evaluated and asexually propagated by basal cuttings taken at the same nursery in Zeeland, Mich., USA in 2015. Evaluation of these and further cutting grown plants shows that *Salvia* 'Perfect Profusion' continues to be stable and produce true to type plants in successive generations of asexual propagation.

SUMMARY OF THE INVENTION

Plants of *Salvia* 'Perfect Profusion' can be most closely compared to: the male parent, *Salvia* 'Crystal Blue', 'Sky Blue Marvel' (not patented), 'Blue Hill' (not patented), 'Bumblesky' U.S. Plant Pat. No. 30,085 and 'Sensation Sky Blue' (not patented). 'Crystal Blue' has broader flowers, less rounded habit and the flowers do not repeat as well after deadheading. 'Sky Blue Marvel' is shorter in habit with much deeper blue flower color, and the repeat flowering is more limited. 'Blue Hill' is more open and slightly taller in habit with less repeat flowering and flower color of darker violet-blue. 'Sensation Sky Blue' is much shorter in habit and has darker violet-blue flowers. The male parent has darker rose-violet flowers and shorter habit. 'Bumblesky' is shorter in habit.

The following characteristics in combination distinguish *Saliva* 'Perfect Profusion' as a new and distinct cultivar from all other cultivars known to the inventor:

1. Narrow pale icy blue flowers densely arranged in verticils;
2. Stiff, upright, heavily-branched flower stems;
3. Strong repeat flowering when deadheaded;
4. Compact, rounded, strong, vigorous and winter-hardy habit;
5. Rugose gray-green foliage.

BRIEF DESCRIPTION OF THE DRAWINGS

The photographs of the new plant demonstrate the unique traits and the overall appearance of *Salvia* 'Perfect Profusion'. The colors are as accurate as reasonably possible with color reproductions. Variation in ambient light spectrum, source and direction may cause the appearance of minor variation in color. The plant used in the photographs was a two-year old plant grown in an open, full-sun trial garden at a wholesale perennial nursery in Zeeland, Mich. with supplemental water and fertilizer when needed.

DETAILED BOTANICAL DESCRIPTION

Figure 1:
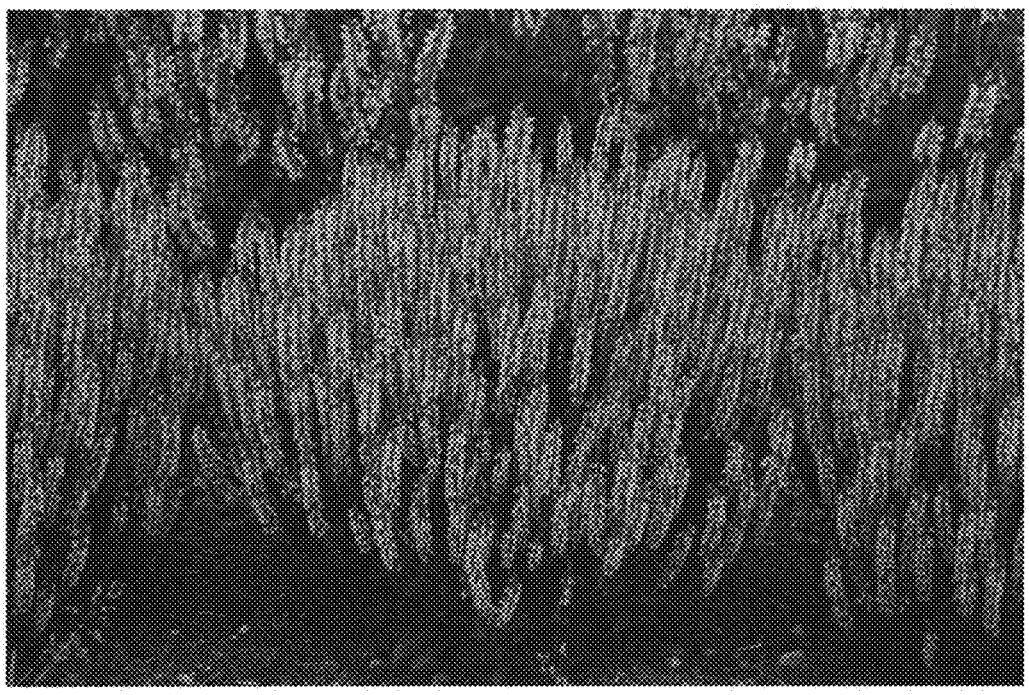
FIG. 1 shows the plant habit in full flower in a landscape.
Figure 2:
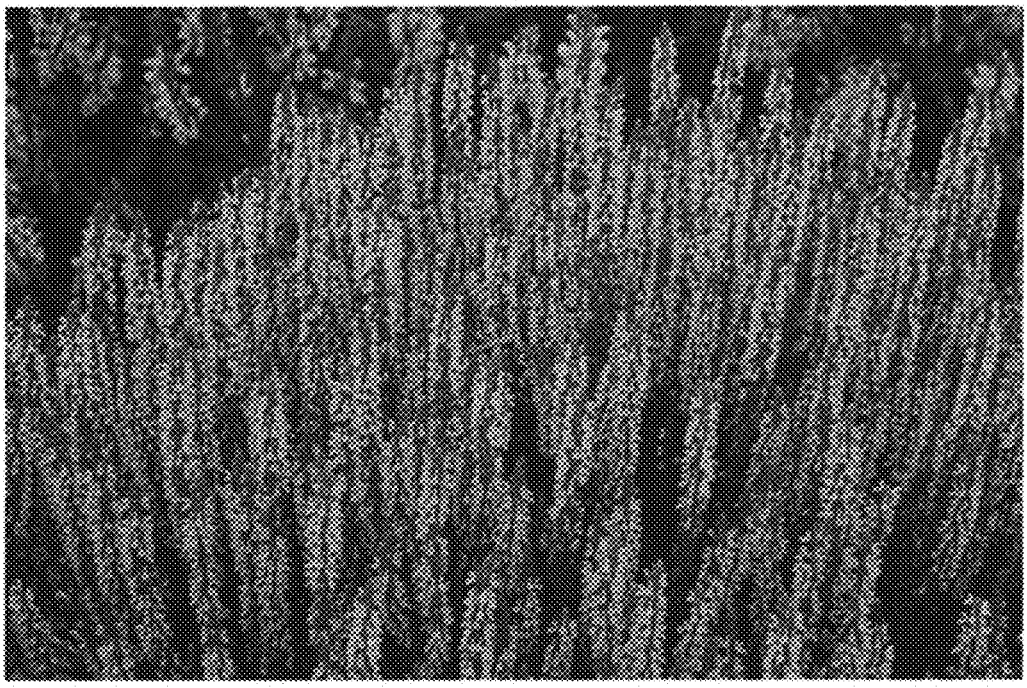
FIG. 2 shows a close-up of the flower scape with the buds, flowers, stems and calyxes.

The following descriptions and color references except where common dictionary terms are used are based on the 2015 edition of The Royal Horticultural Society Colour Chart. *Salvia* 'Perfect Profusion' has not been observed under all possible environments. The phenotype may vary slightly with different growing environments such as temperature, light, fertility, soil pH, moisture and plant maturity levels, but without any change in the genotype. The following observations and size descriptions are based on two-year-old plants growing in an outdoor full-sun trial garden and in a greenhouse at a wholesale perennial nursery in Zeeland, Mich. and greenhouse forced two-year old plants. Plants were given supplemental water and fertilizer.

Botanical classification: *Salvia nemorosa* (Linnaeus);

Parentage: Female or seed parent 'Crystal Blue'; male or pollen parent 'Sensation Deep Rose';

Plant habit: Winter-hardy herbaceous perennial; multi-stemmed, compact, rounded, with mostly basal foliage, and flowers in several, tightly-arranged verticils on highly-branched upright racemes displayed above foliage; flowering to about 51.0 cm tall and about 52.5 cm wide at the fullest point about 25 cm above soil; with cauline foliage below branches;

Propagation: By basal vegetative shoot cuttings; time to produce a rooted stems about two weeks;

Growth rate: Rapid, vigorous, finishing in a 65 mm container in about 7 weeks from rooted cutting, and from 65 mm container to flowering 3.8 liter container in about 8 weeks.

Root description: Fine, well-branched; color dependent on age and soil type, from cream to dark tan in color; typically nearest RHS 161D;

Foliage: Opposite, simple, rugose, lanceolate; margin crenulate; glabrous and matte abaxial and adaxial surfaces; acute apex and base cordate to truncate; leaf blades about 10.2 cm long and 4.7 cm across, decreasing in size distally; average about 7.5 cm long and 2.4 cm across; faint sage fragrance; leaves not variegated;

Foliage color: Adaxial surface between RHS 139A and RHS 137A; abaxial surface nearest RHS 147B;

Venation: Reticulate; impressed on adaxial side and costate on abaxial side; midrib puberulent secondary veins glabrous abaxial; puberulent adaxial;

Vein color: Adaxial midrib nearest RHS 145D, secondary veins nearest RHS 145C; abaxial midrib nearest RHS 145D and primary and secondary veins nearest RHS 148D;

Petiole: Concavo-convex; glabrous adaxial, pubescent abaxial and ciliolate margin; to about 9.5 cm long and 6.0 mm wide, average 4.5 cm long and 4.5 mm wide at base;

Petiole color: Adaxial and abaxial surfaces nearest 145B in center with margin nearest RHS 138A;

Flower description: Perfect, bilabiate, verticillate with flowering generally beginning at lower verticils and advancing up the scape, but not all flowers at each verticil opening at the same time giving the effect of a scape being in continuous flower for longer periods; average distance between verticils about 7.0 mm, greater proximally and less distally; with midline projected about 30 degree angle above horizontal and hood petal about 55 degree angle above horizontal; self-cleaning, petals not persistent; flowering beginning late spring for about six weeks and repeating if initial scapes removed;

Inflorescence description: Total length about 51 cm long, flowering in upper 18 cm and branching to about 9 cm wide; average internode distance in flowering portion about 6.0 mm; number of flowers per node or verticil about 12 in lowest nodes, decreasing distally;

Flower longevity: About four days on the plant or as cut flower;

Fragrance: None detected under present growing conditions;

Flower buds one day prior to anthesis: Shape is rounded on top and slightly concave below, with rounded apex; pubescent; about 8.0 mm long, 3.5 mm tall and 2.5 mm wide;

Bud color: Exposed petals between RHS 92D and RHS 92C; abaxial calyx nearest RHS 137B distally and proximally nearest RHS 138B with veins nearest RHS 137B;

Flowers: Bilabiate corolla with arcuate hooded upper lip and tri-lobed lower lip; about 12.0 mm long, 8.0 mm tall and 4.5 mm wide fused into tube in the proximal 6.5 mm; clustered at verticils with up to 8 flowers per verticil;

Petals: Bilabiate corolla; upper hood petal and flattened side to side vertically, with emarginate apex and base fused with labium in proximal 5.0 mm;

Hood (upper) petal: Minutely pubescent outside, glabrous inside; about 10.0 mm long, 3.5 mm tall and 2.0 mm across;

Labium (lower) petal: Consisting of three lobes, two proximal lobes projecting outwardly, about 2.5 mm long and 1.5 mm wide at base with rounded apex; center lobe reflex, rounded emarginate apex, about 5.0 mm long 8.0 mm wide with a 2.0 mm apical notch at apex; center lobe slightly concaved upwards; total labium about 8.0 mm long, 4.5 mm wide at the widest portion across middle of central lobe and 5.0 mm tall;

Petal color: Abaxial and adaxial hood petal between RHS 92C and RHS 92D; lower labium petal proximal lobes abaxial and adaxial nearest RHS 92D and center lobe abaxial and adaxial nearest RHS 92C;

Androecium: Two, fused with labium, contained within hood petal except when triggered by pollinator;

*Filament*.—Glabrous, fused about 4.0 mm from base of labium petal; curved around inside of hood petal; about 1.5 mm long and less than 0.3 mm diameter with a 1.0 mm trip mechanism at base; color lighter than RHS 92D, trip lever base nearest RHS 92D and tip nearest RHS N88B.

*Anther*.—Glabrous, oblong, about 1.0 mm long and 0.5 mm diameter; longitudinal, dorsifixed; color nearest RHS N84B.

*Pollen*.—Abundant; globose; less than 0.1 mm circumference; color nearest RHS 11C.

Gynoecium: One, curved around inside of hood petal;

*Style*.—About 10.0 mm long and less than 0.5 mm diameter; color nearest RHS NN155D in basal 4.0 mm and gradually darkening distally to nearest RHS 85C about 1.0 mm before stigma split.

*Stigma*.—Bifurcate and curved in the terminal 1.5 mm; apex pointed; color nearest RHS 85C.

*Ovary*.—Superior; color nearest RHS N144A.

Fruit: Nutlet, one to four per flower; rounded, about 1.0 mm diameter; color nearest RHS 202A;

Calyx: Five sepals, three upper and two lower, campanulate; apices acute; fused in basal 3.5 mm; tube about 5.5 mm long and 4.0 mm tall at mouth and 2.5 mm wide; lower set bifurcate in terminal 2.0 mm; upper set of trifurcate in distal 0.5 mm; glandular abaxial and glabrous adaxial;

Calyx color: Nearest RHS 137B distally and proximally nearest RHS 138B with veins nearest RHS 137B;

Bracts: Each verticil subtended by two opposite nearly cordate bracts; apex typically acuminate, base truncate, margin crenate and ciliolate; coarsely wavy to bent downward toward apex; glabrous above and puberulent below; bract size up to 3.0 mm long and 2.8 mm wide, decreasing distally;

Bract color: Adaxial nearest RHS 139A and abaxial nearest RHS 138A with midrib and base nearest RHS 145C;

Peduncles: Raceme; quadrangular in cross section; about 12 per plant; strong; upright; to about 51.0 cm tall and 5.0 mm across at base; pubescent; compound branches in lower two to four nodes, upright at 50 to 60 degrees above horizontal; branches to about 28.0 cm long and 3.0 mm across; average internode distance about 4.5 cm;

Peduncle color: Nearest RHS 138A;

Pedicels: Cylindrical; puberulent to glandular; about 1.5 mm long and 0.5 mm diameter; puberulent to glandular; slightly upwardly at flower anthesis through seed set;

Pedicel color: Nearest RHS 146D;

Disease and pest resistance: Resistant to diseases and pests beyond that common to *Salvia* has not been noted. Specific diseases and pests have not been tested, but the new plant is not commonly browed by *Cervinae* or *Oryctolagus*.

Growth recommendations: Plants of *Salvia* 'Perfect Profusion' perform best with adequate moisture and good drainage and are hardy from USDA zone 3 to 8.

It is claimed:

1. A new and distinct perennial *Salvia* plant named 'Perfect Profusion' as herein described and illustrated useful for landscaping as a specimen plant or en masse.

* * * * *